United States Patent
Niijima et al.

(10) Patent No.: US 11,596,336 B2
(45) Date of Patent: Mar. 7, 2023

(54) LEARNING MODEL-GENERATING APPARATUS, METHOD, AND PROGRAM FOR ASSESSING FAVORED CHEWING SIDE AS WELL AS DETERMINATION DEVICE, METHOD, AND PROGRAM FOR DETERMINING FAVORED CHEWING SIDE

(71) Applicant: NIPPON TELEGRAPH AND TELEPHONE CORPORATION, Tokyo (JP)

(72) Inventors: Arinobu Niijima, Musashino (JP); Takashi Isezaki, Musashino (JP); Ryosuke Aoki, Musashino (JP); Tomoki Watanabe, Musashino (JP); Tomohiro Yamada, Musashino (JP)

(73) Assignee: NIPPON TELEGRAPH AND TELEPHONE CORPORATION, Tokyo (JP)

(*) Notice: Subject to any disclaimer, the term of this patent is extended or adjusted under 35 U.S.C. 154(b) by 172 days.

(21) Appl. No.: 17/059,039

(22) PCT Filed: May 22, 2019

(86) PCT No.: PCT/JP2019/020322
§ 371 (c)(1),
(2) Date: Nov. 25, 2020

(87) PCT Pub. No.: WO2019/230528
PCT Pub. Date: Dec. 5, 2019

(65) Prior Publication Data
US 2021/0212621 A1 Jul. 15, 2021

(30) Foreign Application Priority Data
May 30, 2018 (JP) .............................. JP2018-103580

(51) Int. Cl.
*A61B 5/00* (2006.01)
*A61B 5/22* (2006.01)
(Continued)

(52) U.S. Cl.
CPC .............. *A61B 5/228* (2013.01); *A61B 5/389* (2021.01); *A61B 5/397* (2021.01); *A61B 5/7264* (2013.01); *A61B 5/7207* (2013.01)

(58) Field of Classification Search
CPC ......... A61B 5/224; A61B 5/228; A61B 5/316; A61B 5/389; A61B 5/395; A61B 5/397;
(Continued)

(56) References Cited

U.S. PATENT DOCUMENTS

2011/0313310 A1* 12/2011 Tomita ................. A61B 5/7257
600/546

FOREIGN PATENT DOCUMENTS

JP 2019184528 A * 10/2019

OTHER PUBLICATIONS

Zamanlu, Masumeh, et al. "Chewing side preference in first and all mastication cycles for hard and soft morsels." International journal of clinical and experimental medicine 5.4 (2012): 326. (Year: 2012).*

(Continued)

*Primary Examiner* — David J. McCrosky
*Assistant Examiner* — Nidhi N Patel (57) ABSTRACT

A reliable technology for determining the masticatory side of the user is provided. First and second electromyographic waveforms respectively originating from left and right muscles related to masticatory actions of a user are acquired; a coefficient of correlation between pieces of information respectively extracted from the first and the second electromyographic waveforms is calculated as a first feature value; a second feature value is calculated from a power spectrum obtained by performing frequency analysis on the first electromyographic waveform; a third feature value is calculated from a power spectrum obtained by performing frequency analysis on the second electromyographic wave-
(Continued)

form; a learning model is generated by associating the first, second, and third feature values with a plurality of labels; and the masticatory side of the user is determined based on first, second, and third feature values calculated from a newly acquired electromyographic waveform and the learning model.

5 Claims, 6 Drawing Sheets

(51) Int. Cl.
*A61B 5/389* (2021.01)
*A61B 5/397* (2021.01)

(58) Field of Classification Search
CPC ... A61B 5/4557; A61B 5/4542; A61B 5/7207; A61B 5/7264
See application file for complete search history.

(56) References Cited

OTHER PUBLICATIONS

English Machine Translation of Fujiwara (JP 2019184528 A) (Year: 2019).*
Yo Yamasaki et al., Objective assessment of actual chewing side by measurement of bilateral masseter muscle electromyography, Archives of Oral Biology, vol. 60, No. 12, 2015, pp. 1756-1762.

* cited by examiner

| RESULTS OF DETERMINATION | TASK2 | TASK3 | TASK4 | TASK5 |
|---|---|---|---|---|
| MYOELECTRIC POTENTIAL | 91% | 88% | 0% | 0% |
| NOISE | 9% | 12% | 100% | 100% |

Fig. 6

| | | ESTIMATED LABEL | | |
|---|---|---|---|---|
| | | BILATERAL MASTICATION | RIGHT SIDE MASTICATION | LEFT SIDE MASTICATION |
| CORRECT LABEL | BILATERAL MASTICATION | 98.5% | 0.7% | 0.8% |
| | RIGHT SIDE MASTICATION | 0.7% | 98.7% | 0.6% |
| | LEFT SIDE MASTICATION | 0.5% | 0.7% | 98.8% |

LEARNING MODEL-GENERATING APPARATUS, METHOD, AND PROGRAM FOR ASSESSING FAVORED CHEWING SIDE AS WELL AS DETERMINATION DEVICE, METHOD, AND PROGRAM FOR DETERMINING FAVORED CHEWING SIDE

CROSS-REFERENCE TO RELATED APPLICATIONS

This application is a 371 U.S. National Phase of International Application No. PCT/JP2019/020322, filed on May 22, 2019, which claims priority to Japanese Application No. 2018-103580 filed on May 30, 2018. The entire disclosures of the above applications are incorporated herein by reference.

Technical Field

One aspect of the present invention relates to a learning model generation apparatus for determining the masticatory side of a user, a method and a program for the same, a masticatory side determination apparatus, and a method and a program for the same.

BACKGROUND ART

In masticatory activities such as eating, humans may chew food on one of the left or right side more than the other due to pain caused by cavities or the like or due to the dominant side of the jaw. The side mainly used in mastication is called the masticatory side, and on-sided mastication is called unilateral mastication. Such unilateral mastication may cause jaw distortion, which may lead to facial distortion, temporomandibular joint disorder, and even stiff shoulders and headaches. Therefore, in order for early detection of unilateral mastication, it may be useful to understand the user's masticatory habits in daily life.

A method of measuring left and right muscle activities during mastication is known as a simple method for estimating mastication habits (see NPL 1). For example, when disposable electrodes are placed on the left and right masticatory muscles (masseter or temporalis muscle) to measure the myoelectric potential, the amplitude of the myoelectric potential on the right side increases when mastication is performed on the right side, and the amplitude of the myoelectric potential on the left side increases when mastication is performed on the left side.

CITATION LIST

Non Patent Literature

[NPL 1] Yo Yamasaki et al., "Objective assessment of actual chewing side by measurement of bilateral masseter muscle electromyography", Archives of Oral Biology, Volume 60, Issue 12, December 2015, Pages 1756-1762

SUMMARY OF THE INVENTION

Technical Problem

However, when muscle activities are monitored on a daily basis for a long period of time to estimate mastication habits, noise contamination may significantly affect the results of estimation. For example, it is known that the value (potential) to be measured by a myoelectric sensor changes if the body or the electrodes are replaced. If such a value is analyzed as the myoelectric potential, the reliability of the results of estimation may degrade. Such an effect is particularly noticeable when cloth electrodes are used for long-term monitoring instead of disposable electrodes.

In addition, the amplitude of the myoelectric potential changes depending on the contact impedance between the skin and the electrodes (skin impedance). Skin impedance easily changes due to the humidity of the outside air and human sweat. Therefore, if the amplitude of the myoelectric potential is used as an indicator when determining the masticatory side, it is possible to make an erroneous determination due to such factors.

The present invention has been made in view of the foregoing, and an object of the present invention is to provide a reliable technology for determining the masticatory side of a user based on the surface myoelectric potential of the masticatory muscles.

Means for Solving the Problem

To solve the above-described problem, one aspect of the present invention provides a learning model generation apparatus that is configured to: acquire first and second electromyographic waveforms respectively originating from left and right muscles related to masticatory actions of a user; calculate a coefficient of correlation between pieces of information respectively extracted from the first and the second electromyographic waveforms, as a first feature value for learning; calculate a second feature value for learning, from a power spectrum obtained by performing frequency analysis on the first electromyographic waveform; calculate a third feature value for learning, from a power spectrum obtained by performing frequency analysis on the second electromyographic waveform; and generate a learning model by associating the first, second, and third feature values for learning with a plurality of labels for specifying a masticatory side of the user.

A second aspect of the present invention is a masticatory side determination apparatus that determines a masticatory side of a user by using a learning model generated by the learning model generation apparatus according to the above-described first aspect, the masticatory side determination apparatus being configured to: acquire first and second electromyographic waveforms respectively originating from left and right muscles related to masticatory actions of the user; calculate a coefficient of correlation between pieces of information respectively extracted from the first and the second electromyographic waveforms, as a first feature value for determination; calculate a second feature value for determination, from a power spectrum obtained by performing frequency analysis on the first electromyographic waveform; calculate a third feature value for determination, from a power spectrum obtained by performing frequency analysis on the second electromyographic waveform; and determine the masticatory side of the user with reference to the learning model, based on the first, second, and third feature values for determination.

A third aspect of the present invention is the second aspect configured to further perform abnormal value determination to determine whether the first, second, and third feature values for determination are normal values or abnormal values for each predetermined unit time range, based on the first, the second, and the third feature values for determination, and perform masticatory side determination only for a unit time range in which the feature values are determined as normal values.

A fourth aspect of the present invention is the third aspect configured to use an unsupervised learning model to perform the abnormal value determination.

Effects of the Invention

According to the first aspect of the present invention, a correlation coefficient regarding electromyographic waveforms respectively originating from left and right masticatory muscles of the user, and values calculated from power spectra obtained by performing frequency analysis on the electromyographic waveforms respectively originating from the left and right masticatory muscles, are employed as feature values for learning, and a learning model is generated by associating these feature values with labels for specifying the masticatory side of the user. As described above, feature values that are relatively robust to changes in skin impedance are used to generate the learning model, instead of the amplitude of the myoelectric potential that is susceptible to the skin impedance. Therefore, it is possible to obtain a reliable learning model that is less likely to be affected by measurement conditions.

According to the second aspect of the present invention, the masticatory side is determined based on the labels by referencing the learning model generated as described above, and using, as feature values for determination, the correlation coefficient regarding electromyographic waveforms respectively originating from left and right masticatory muscles of the user, and values calculated from power spectra obtained by performing frequency analysis on the electromyographic waveforms respectively originating from the left and right masticatory muscles. As described above, feature values that are relatively robust to changes in skin impedance are used as feature values used to generate a learning model and perform class determination. Therefore, it is possible to obtain reliable results of determination with a reduced probability of making an erroneous determination due to changes in skin impedance.

According to the third aspect of the present invention, determination is performed to discern between normal values and abnormal values, for each unit time range, based on the above-described three feature values, and the determination of the masticatory side is performed only for data in the unit time range in which the feature values are determined as normal values. As described above, feature values that are relatively robust to changes in skin impedance are used. Therefore, it is possible to improve the reliability of abnormality detection. As a result, it is also possible to only use data determined as normal values (i.e. originating from electromyography) in each unit time range to determine the masticatory side, while excluding data determined as abnormal values (i.e. noise). Therefore, it is possible to realize more reliable masticatory side determination with a further reduced probability of making an erroneous determination due to noise. In addition, it is possible to minimize the target data that is used to determine the mastication side, and therefore it is also possible to reduce the processing load on the system.

According to the fourth aspect of the present invention, the above-described abnormal value determination is performed using an unsupervised learning model. As a result, it is possible to easily discern between abnormal values and normal values, using machine learning, without labeling the feature values in advance, even for data that is difficult for humans to determine whether it is a normal value or an abnormal value. As a result, it is possible to realize reliable masticatory side determination that can decern abnormal values included in the target data and exclude abnormal values from the target of analysis, without performing complex processing.

That is to say, each aspect of the present invention can provide a reliable technology for determining the masticatory side of the user based on the surface myoelectric potentials of the masticatory muscles.

DESCRIPTION OF EMBODIMENTS

Hereinafter, an embodiment according to the present invention will be described with reference to the drawings.

Embodiment (Configuration)

Figure 1:
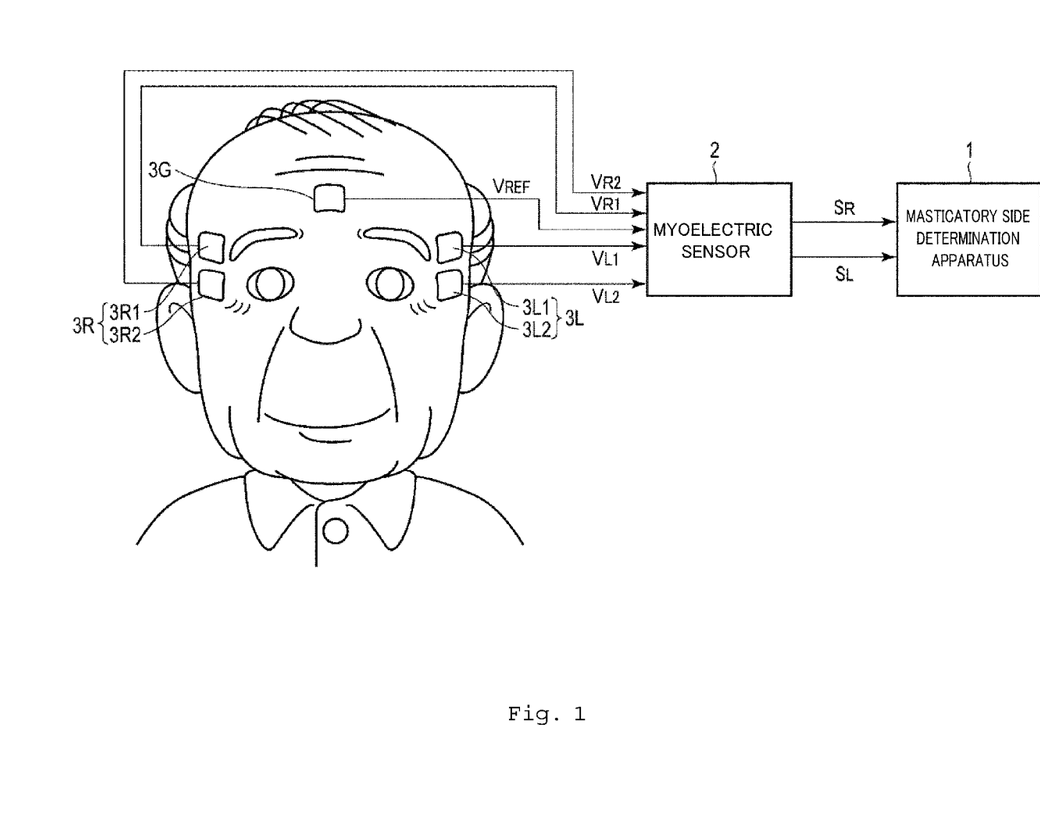
FIG. 1 is an overall configuration diagram showing a system that includes a masticatory side determination apparatus according to one embodiment of the present disclosure.

FIG. 1 is an overall configuration diagram showing a system that includes a masticatory side determination apparatus according to one embodiment of the present invention. This system includes a masticatory side determination apparatus 1, a myoelectric sensor 2, and electrodes 3L1, 3L2, 3R1, 3R2, and 3G.

As shown in FIG. 1, according to one embodiment, electrodes 3L1 and 3L2 and electrodes 3R1 and 3R2 are attached to the skin surfaces on the left temporalis muscle and the right temporalis muscle of the user, respectively, and the ground electrode 3G is attached to the surface of a central portion of the forehead of the user. The left temporalis muscle and the right temporalis muscle are one type of muscle for performing masticatory actions, for example, and are located near the temples.

Generally, surface electromyography (sEMG) shows changes over time in the potential difference between two electrodes that are placed so as to extend in the direction in which muscle fibers run. The distance between these two electrodes is set to the range of approximately 20 mm to 40 mm depending on the size of the muscle to be measured. The position at which the ground electrode 3G is to be placed does not need to be strictly determined, and the ground electrode 3G is generally placed on the skin on a part in which there is no muscle.

The electrodes 3L1 and 3L2 (collectively referred to as the "electrodes 3L") and the electrodes 3R1 and 3R2 (collectively referred to as the "electrodes 3R") are constituted by cloth electrodes with an electrode size of 30 mm×30 mm, and output potential signals that represent the muscle activities of the left temporalis muscle and the right temporalis muscle, as VL1, VL2, VR1, and VR2 (collectively referred to as the "myoelectric potential signals V"). The ground electrode 3G outputs a signal VREF that represents a reference potential. These myoelectric potential signals V and reference potential signal VREF are transmitted to a myoelectric sensor 2 via signal cables, for example.

Note that a wireless unit that conforms to a low power wireless data communication standard such as Bluetooth (registered trademark) may be attached to the electrodes 3L, 3R, and 3G, and thus the myoelectric potential signals V and the reference potential signal VREF may be supplied to the myoelectric sensor 2. Also, the positions to which the electrodes 3L and 3R are attached may be freely selected on the left and right masticatory muscles, and furthermore, there is no limitation on the size, shape, and material of the electrodes 3L, 3R, and 3G, or the means for attaching the same, for example, as long as surface electromyography can be measured. Also, the electrodes 3L, 3R, and 3G may be integrated with a preamplifier.

The myoelectric sensor 2 performs predetermined processing on the myoelectric potential signals V and the reference potential signal VREF measured using the electrodes 3L, 3R, and 3G, and outputs the results to the masticatory side determination apparatus 1. For example, the myoelectric sensor 2 acquires signals representing surface electromyograms for the left and right sides from the potential difference between the myoelectric potential signals VL1 and VL2 and the potential difference between the myoelectric potential signals VR1 and VR2, based on the left and right myoelectric potential signals VL1, VL2, VR1, and VR2 and the reference potential signal VREF input to the myoelectric sensor 2, amplifies the signals (e.g. by an amplification factor of 1000), performs band-pass filtering, performs A/D conversion, and can thus output the signals as digital signals SL and SR to the masticatory side determination apparatus 1. Note that the myoelectric sensor 2 need not necessarily be an independent apparatus, and may be integrated with the electrodes 3L, 3R, and 3G, or with the masticatory side determination apparatus 1.

Figure 2:
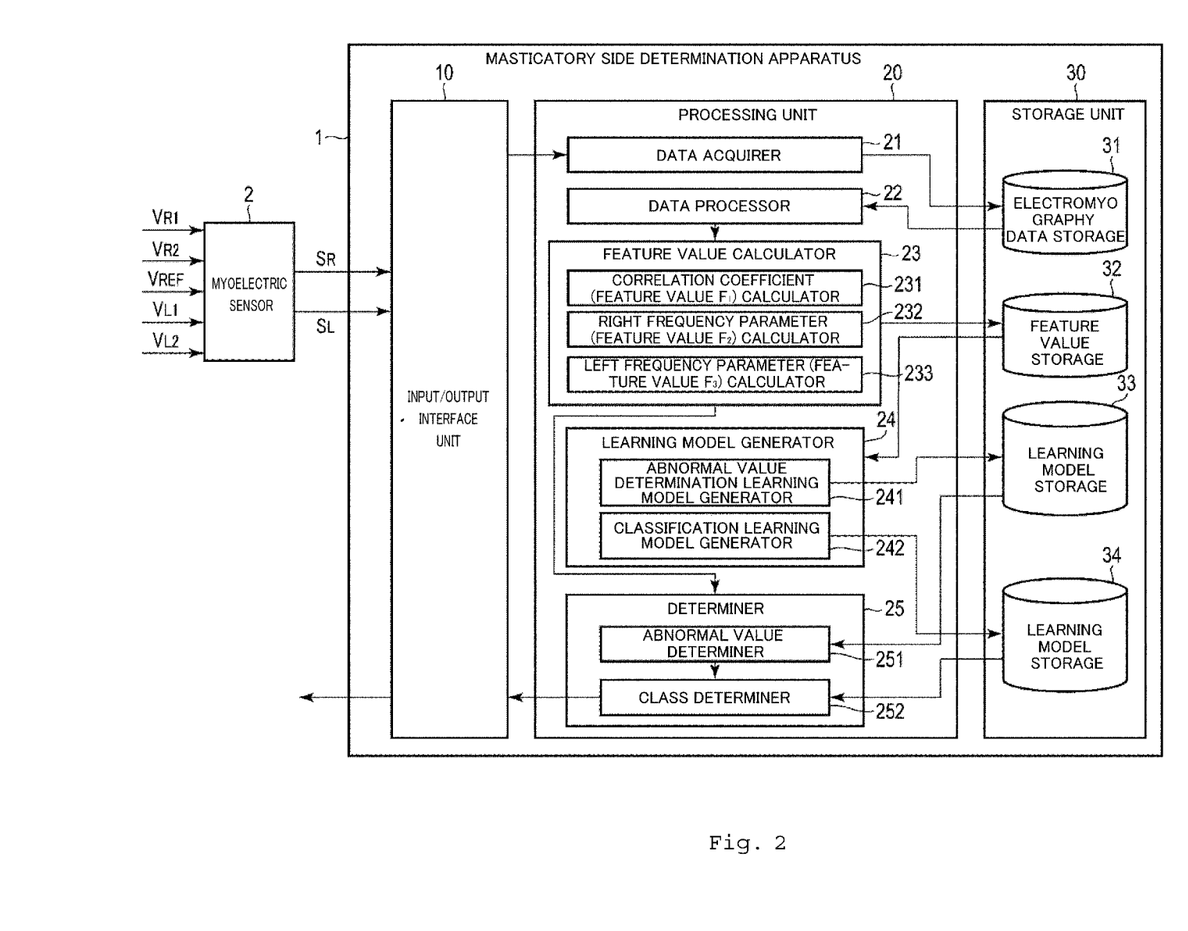
FIG. 2 is a block diagram showing a functional configuration of a masticatory side determination apparatus according to one embodiment of the present disclosure.

The masticatory side determination apparatus 1 is realized using a personal computer, for example, and is configured as described below. FIG. 2 is a block diagram showing hardware and software functional configurations thereof.

The masticatory side determination apparatus 1 includes an input/output interface unit 10, a processing unit 20, and a storage unit 30.

The input/output interface unit 10 receives the digital signals SL and SR output from the myoelectric sensor 2 and outputs the signals to the processing unit 20 as electromyography data (hereinafter also referred to as "electromyographic waveforms"). The input/output interface unit 10 also has the function of outputting the result of determination output from the processing unit 20, to an external device. An example of the external device is an information processing apparatus such as a user terminal equipped with a display, or a personal computer, a server, or the like that determines the user's masticatory actions based on measurement data.

The storage unit 30 is realized using, as a storage medium, a non-volatile memory that is writable and readable at any time, such as an HDD (Hard Disk Drive) or an SSD (Solid State Drive), and a volatile memory such as a RAM. The storage area of the storage unit 30 includes, in addition to a program storage, an electromyography data storage 31, a feature value storage 32, a learning model storage 33 for abnormal value determination, and a learning model storage 34 for classification.

The electromyography data storage 31 stores electromyography data that has been acquired, in time series. The electromyography data storage 31 can also store information that specifies the state of the user's mastication (the masticatory side) as of the acquisition of electromyography data, input by the user via an input unit (not shown), for example.

The feature value storage 32 stores feature values calculated based on electromyography data. The feature value storage 32 can also store the calculated feature values in association with information that specifies the masticatory side.

The learning model storage 33 for abnormal value determination stores a learning model for abnormal value determination that has been generated based on the aforementioned feature values, and is referenced when abnormal value determination processing is performed.

The learning model storage 34 for classification stores a learning model for classification that has been generated based on the aforementioned feature value and information specifying the masticatory side, and is referenced when classification processing for determining the masticatory side is performed.

The processing unit 20 includes a hardware processor such as a CPU (Central Processing Unit) and a memory, which are not shown, and includes a data acquirer 21, a data processor 22, a feature value calculator 23, a learning model generator 24, and a determiner 25, as necessary processing functions for implementing the present embodiment. All of these processing functions are realized by causing the aforementioned processor to execute programs stored in the aforementioned storage unit 30.

The data acquirer 21 performs processing to retrieve pieces of electromyography data that indicate movement of the aforementioned left and right temporalis muscles from the input/output interface unit 10, and store these pieces of electromyography data in the electromyography data storage 31 in time series. At this time, the data acquirer 21 can also acquire information that specifies the user's masticatory side as of the measurement of the myoelectric potential, input by the user of the masticatory side determination apparatus 1 or an operator via an input unit (not shown), for example. This information is stored in the electromyography data storage 31 in association with electromyography data, and can be used later as correct answer labels in supervised learning.

The data processor 22 reads out electromyography data from the electromyography data storage 31, and performs predetermined processing. For example, the data processor 22 has a band-pass filtering function to which a frequency passband has been set in advance in order to remove noise components generated due to body movements or the like. By performing the aforementioned band-pass filtering on the electromyography data read out from the aforementioned electromyography data storage 31, the data processor 22 removes noise components generated due to body movements or the like from the aforementioned data.

The feature value calculator 23 performs processing to set windows that each have a predetermined time width to the electromyography data that has undergone filtering performed by the aforementioned data processor 22, calculate feature values of the electromyographic waveforms in each window, and store the calculated feature values in the feature value storage 32. In the present embodiment, the feature value calculator 23 includes a correlation coefficient (feature value F1) calculator 231, a right frequency parameter (feature value F2) calculator 232, and a left frequency parameter (feature value F3) calculator 233. The three calculated feature values F1, F2, and F3 are stored in the feature value storage 32. At this time, the feature values F1, F2, and F3 may be stored in association with information that specifies the user's masticatory side.

The correlation coefficient calculator 231 performs root mean square (RMS) processing on the electromyographic waveforms of the left and right temporalis muscles for each window that has the aforementioned predetermined time width, and thereafter performs processing to calculate, as the feature value F1, a correlation coefficient that indicates the correlation between pieces of information extracted from the left and right electromyographic waveforms. For example, the correlation coefficient calculator 231 calculates, as the feature value F1, a cross-coefficient of correlation between the absolute values of the left and right myoelectric potentials from the electromyographic waveforms that have undergone RMS processing, for the constant window range that has been set in advance.

The right frequency parameter calculator 232 performs frequency analysis on the electromyographic waveform acquired via the electrode 3R on the right temporalis muscle, and performs processing to calculate the feature value F2 from the power spectrum obtained through the frequency analysis. For example, the right frequency parameter calculator 232 calculates, as the feature value F2, a median power frequency (MF) from the power spectrum of the electromyographic waveform of the right temporalis muscle.

The left frequency parameter calculator 233 performs frequency analysis on the electromyographic waveform acquired via the electrode 3L on the left temporalis muscle, and performs processing to calculate the feature value F3 from the power spectrum obtained through the frequency analysis. For example, the left frequency parameter calculator 233 calculates, as the feature value F3, a median power frequency from the power spectrum of the electromyographic waveform of the left temporalis muscle.

The learning model generator 24 generates learning models based on the feature values F1 to F3 calculated by the feature value calculator 23 and stored in the feature value storage 32, and includes an abnormal value determination learning model generator 241 and a classification learning model generator 242.

The abnormal value determination learning model generator 241 performs processing to generate a learning model for abnormal value determination based on the feature values F1 to F3, and store the learning model in the learning model storage 33 for abnormal value determination.

The learning model generator 242 for classification performs processing to generate a learning model for classification, which is referenced when the masticatory side is to be determined, based on the feature values F1 to F3 and information that specifies the masticatory side and is associated with the feature values, and store the learning model in the learning model storage 34 for classification.

The determiner 25 performs determination based on newly acquired data by referencing learning models that have been generated in advance, and includes an abnormal value determiner 251 and a class determiner 252.

The abnormal value determiner 251 performs abnormal value determination processing for each of the predetermined unit windows, by referencing the learning model for abnormal value determination stored in the learning model storage 33 for abnormal value determination, based on the feature values F1 to F3 calculated from newly measured electromyography data (electromyographic waveforms). For example, the abnormal value determiner 251 can use an abnormality detection (outlier detection) algorithm such as a one-class support vector machine (One-Class SVM) to determine whether the newly acquired data is a normal value or an abnormal value.

The class determiner 252 performs class determination, i.e. processing for determining the masticatory side, for each unit window, by referencing the learning model for classification stored in the learning model storage 34 for classification, based on the feature values F1 to F3 calculated from the newly measured electromyography data (electromyographic waveforms). For example, the class determiner 252 can use class determination such as a k-nearest neighbors algorithm to determine to which class (e.g. bilateral mastication, right side mastication, or left side mastication) the newly acquired data belongs.

Operations

The following describes operations performed by the masticatory side determination apparatus 1 with the above-described configuration to generate learning models and to determine the masticatory side.

(1) Generation of Learning Models

First, the masticatory side determination apparatus 1 performs processing to generate learning models based on the feature values calculated from the electromyography data. Here, the learning model for abnormal value determination, which is used to detect an abnormality, and the learning model for classification, which is used to determine the class, are generated as learning models.

(1-1) Acquisition of Learning Data (1-1-1) Measurement of Surface Electromyography As illustrated in FIG. 1, the two pairs of cloth electrodes 3L1 and 3L2, and 3R1 and 3R2, are attached to the skins on the left and right temporalis muscles of the user, and the ground electrode 3G is attached to the skin on a central portion of the forehead of the user. For the purpose of labeling, conditions such as bilateral mastication with chewing gum being placed on the left and right sides of the user's mouth, unilateral mastication with chewing gum being placed on only the right side, unilateral mastication with chewing gum being placed on only the left side, etc. are set, for example, and the user is caused to perform masticatory actions. The surface muscle potentials VL1, VL2, VR1, VR2, and VREF detected by the electrodes under these conditions are subjected to predetermined processing such as amplification, filtering, and analog/digital conversion performed by the myoelectric sensor 2, and are output to the masticatory side determination apparatus 1 as the digital signals SL and SR respectively representing left and right electromyography data. Note that the aforementioned masticatory conditions may be input to the masticatory side determination apparatus 1 by the user via an input unit (not shown), for example, and stored together with time information in association with data or feature values.

Figure 3:
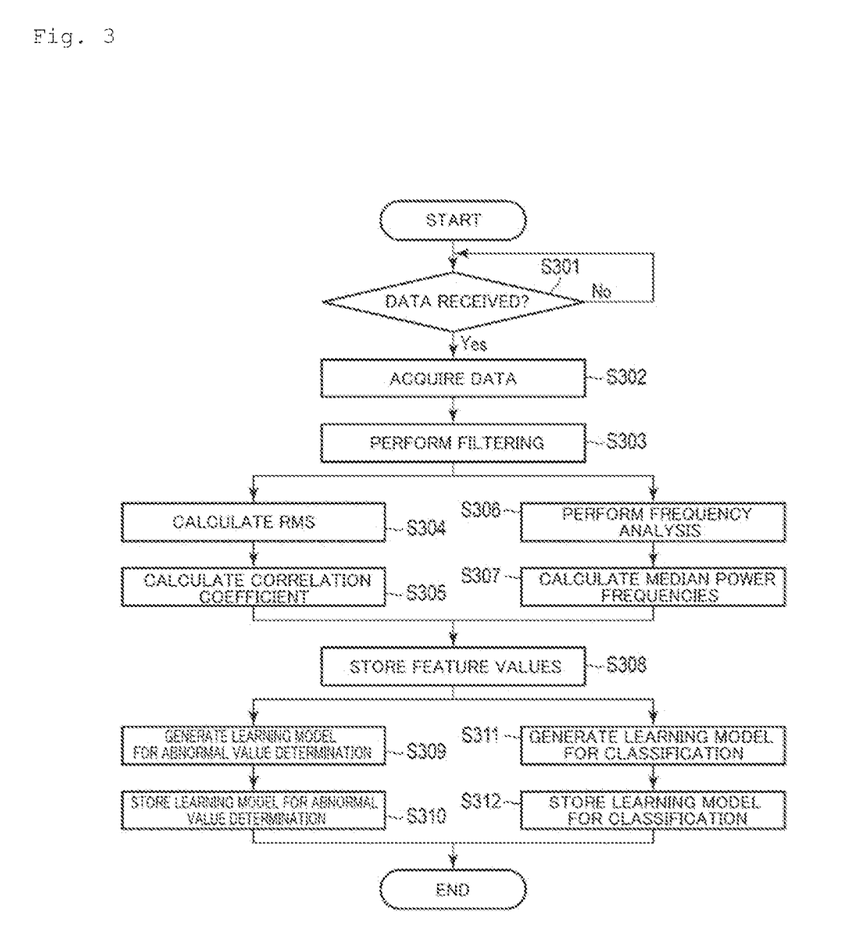
FIG. 3 is a flowchart showing a procedure for generating learning models and the content of processing performed by the masticatory side determination apparatus shown in FIG. 2.

FIG. 3 is a flowchart showing a processing procedure for generating learning models and the content of processing performed by the masticatory side determination apparatus 1 according to an embodiment.

The processing unit 20 of the masticatory side determination apparatus 1 monitors whether or not electromyography data has been received, using step S301. In this state, upon electromyography data being transmitted from the myoelectric sensor 2, the masticatory side determination apparatus 1, in step S302, sequentially retrieves the digital signals SL and SR from the input/output interface unit 10 during a predetermined period of time, under the control of the data acquirer 21, and stores the signals in the electromyography data storage 31 in time series. For example, the data acquirer 21 samples the signals SL and SR at a sampling rate of 1000 Hz.

Next, in step S303, the processing unit 20 of the masticatory side determination apparatus 1 reads out pieces of electromyography data corresponding to the left and right temporalis muscles from the aforementioned electromyography data storage 31, and performs predetermined processing such as band-pass filtering on the pieces of data, under the control of the data processor 22. At this time, the pass band of band-pass filtering is set to 20 Hz to 450 Hz, for example. As a result, the data processor 22 removes noise components that are included in bands other than the band of 20 Hz to 450 Hz and are irrelevant to masticatory actions.

(1-1-2) Calculation of Feature Values

Next, the masticatory side determination apparatus 1 calculates feature values under the control of the feature value calculator 23. In this embodiment, the following three feature values are calculated.

F1: a coefficient of correlation between the absolute values of the left and right myoelectric potentials in a constant window range.

F2: the median power frequency of the power spectrum of the right myoelectric potential in the constant window range.

F3: the median power frequency of the power spectrum of the left myoelectric potential in the constant window range.

In step S304, under the control of the correlation coefficient calculator 231, the masticatory side determination apparatus 1 sets windows of 100 milliseconds (ms) to the pieces of electromyography data corresponding to the left and right temporalis muscles, which have undergone filtering performed by the aforementioned data processor 22, and calculates the respective root mean squares (RMSs) of the aforementioned pieces of data for each of the windows.

Next, in step S305, the masticatory side determination apparatus 1 calculates, as the feature value F1, the coefficient of cross-correlation between the left and right RMSs for each time window of two seconds (2 s) described above, under the control of the correlation coefficient calculator 231.

This feature value F1 is based on the fact that the left and right temporomandibular joints move at the same time. It is envisaged that the left and right electromyographic waveforms generated due to muscle activities have a similar shape and the correlation coefficient is high, whereas the left and right waveforms of potential changes generated due to noise have different shapes and the correlation coefficient is low.

The feature value calculator 23 of the masticatory side determination apparatus 1 can calculate the feature values F2 and F3 after carrying out steps S304 and S305 for calculating the aforementioned feature value F1, or in parallel with steps S304 and S305, or before carrying out steps S304 and S305.

In step S306, the masticatory side determination apparatus 1 performs frequency analysis such as fast Fourier transform (FFT) on each of the left and right pieces of electromyography data under the control of the right frequency parameter calculator 232 and the left frequency parameter calculator 233, to obtain the respective power spectra thereof.

Next, in step S307, the right frequency parameter calculator 232 and the left frequency parameter calculator 233 respectively calculate median power frequencies (MFs) that are representative values of the aforementioned power spectra, as the feature values F2 and F3. A median power frequency is a frequency that halves the area of a power spectrum. Note that the feature values calculated from the power spectra are not limited to median power frequencies, and mean power frequencies (MPFs) may be used, for example.

The calculation of the feature value F2 by the right frequency parameter calculator 232 and the calculation of the feature value F3 by the left frequency parameter calculator 233 may be performed simultaneously or sequentially.

The feature values F1, F2, and F3 calculated through the above-described processing are stored in the feature value storage 32 in step S308 together with time information. At this time, as described above, the feature values F1, F2, and F3 may be stored in association with information that specifies the masticatory side, such as masticatory conditions input in advance.

(1-2) Learning Model

Next, the masticatory side determination apparatus 1 generates the following learning models based on the feature values F1, F2, and F3.

(1-2-1) Learning Model for Abnormal Value Determination

First, in step S309, the masticatory side determination apparatus 1 reads out the feature values F1, F2, and F3 from the feature value storage 32 and generate a learning model for abnormal value determination based on these feature values, under the control of the abnormal value determination learning model generator 241. In this embodiment, the masticatory side determination apparatus 1 may employ unsupervised learning, and use the One-Class SVM as a machine learning algorithm, for example. A One-Class SVM is a method of performing learning using only normal data to estimate an area that includes normal data. If new data is in this area, the masticatory side determination apparatus 1 determines that the data is a normal value, and if new data is out of this area, the masticatory side determination apparatus 1 determines that this data is an abnormal value. Therefore, the masticatory side determination apparatus 1 can measure myoelectric potential data generated due to masticatory muscle activities, in advance as described above, and generate a learning model, using the feature values F1, F2, and F3 calculated from the myoelectric potential data, as learning data.

In step S310, the abnormal value determination learning model generator 241 stores the generated learning model in the learning model storage 33 for abnormal value determination.

(1-2-2) Learning Model for Classification

In step S311, in parallel with steps S309 and S310, or sequentially, the masticatory side determination apparatus 1 reads out the feature values F1, F2, and F3 from the feature value storage 32 and generates a learning model for class determination under the control of the classification learning model generator 242. In this embodiment, the masticatory side determination apparatus 1 may employ supervised learning, and use the k-nearest neighbors algorithm as a machine learning algorithm, for example. The k-nearest neighbors algorithm is a method by which pieces of learning data (templates) are plotted on the vector space, any K templates are selected in ascending order of the distance from the new data, and the class to which the new data belongs is estimated based on the class to which the largest number of templates of the K templates belong. Therefore, the masticatory side determination apparatus 1 measures, in advance, myoelectric potential data generated due to masticatory muscle activities, under such conditions that the masticatory side can be specified, as described above, and thus the masticatory side determination apparatus 1 can generate a learning model, using the feature values F1, F2, and F3 calculated from the myoelectric potential data, together with the label that specifies the masticatory side.

In step S312, the classification learning model generator 242 stores the generated learning model in the learning model storage 34 for classification.

Although the same feature value is used to generate the learning model for abnormal value determination and the learning model for classification in the above embodiment, the present invention is not limited to such a configuration, and feature values that are different from each other may be used to generate the models. Also, algorithms that are used to generate the learning models are not limited to the above examples, and any algorithm may be used.

(2) Determination Performed Using Learning Models

Next, the masticatory side determination apparatus 1 performs processing to determine an abnormal value and the masticatory side with reference to the generated learning models, based on the feature values calculated based on the newly acquired data.

(2-1) Acquisition of Determination Data (2-1-1) Measurement of Surface Electromyography The acquisition of electromyography data for determination and the calculation of feature values can be performed in the same manner as the acquisition of learning data described in (1) above.

That is to say, first, as illustrated in FIG. 1, the two pairs of cloth electrodes 3L1 and 3L2, and 3R1 and 3R2, are attached to the skins on the left and right temporalis muscles of the user, and the ground electrode 3G is attached to the skin on a central portion of the forehead of the user. The surface muscle potentials VL1, VL2, VR1, VR2, and VREF detected by the electrodes are subjected to predetermined processing such as amplification, filtering, and analog/digital conversion performed by the myoelectric sensor 2, and are output as the digital signals SL and SR respectively representing left and right electromyography data. Because they are pieces of data for determination, masticatory conditions are not set unlike in the case of the acquisition of learning data.

Figure 4:
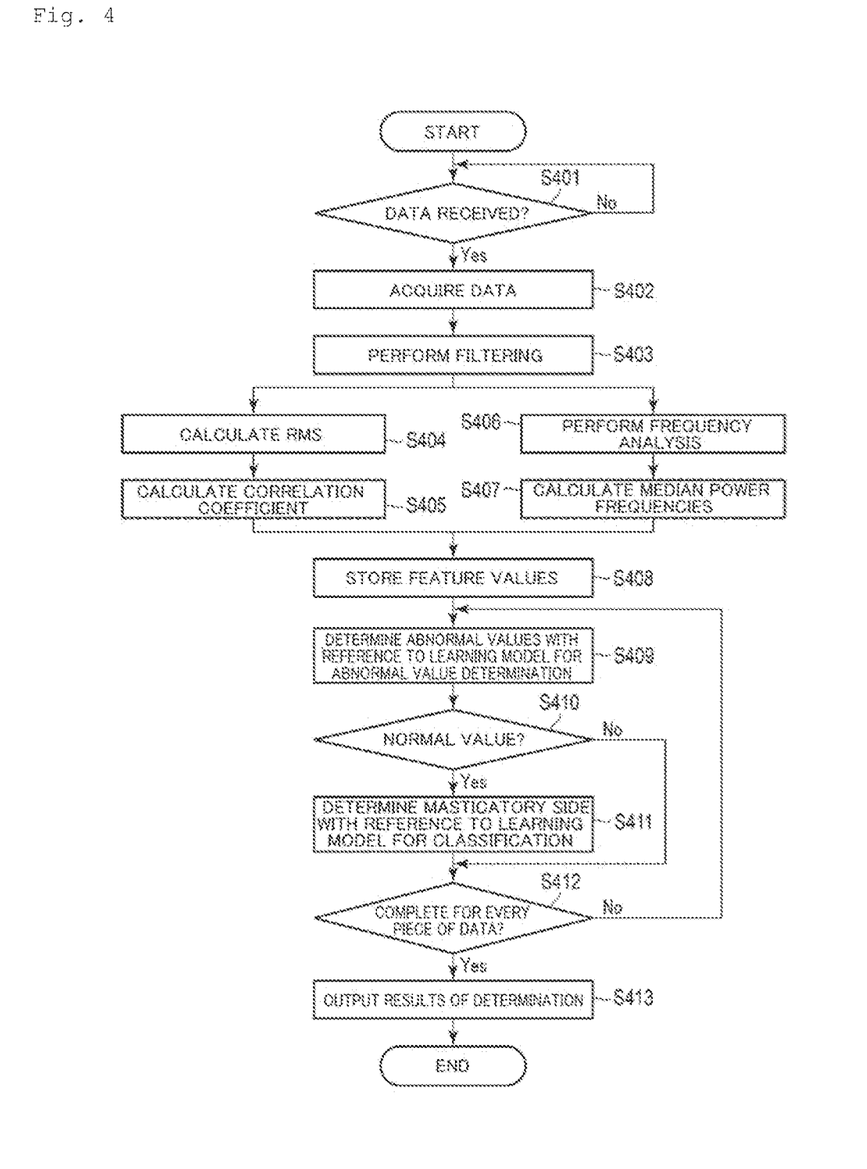
FIG. 4 is a flowchart showing the procedure for determining the masticatory side and the content of processing performed by the masticatory side determination apparatus shown in FIG. 2.

FIG. 4 is a flowchart showing a procedure for abnormal value determination and class determination and the content of processing performed by the masticatory side determination apparatus 1 according to one embodiment. Note that steps S401 to S408 will not be described in detail because they are the same as steps S301 to S308 described with reference to FIG. 3.

First, the processing unit 20 of the masticatory side determination apparatus 1 monitors whether or not electromyography data has been received, using step S401. In this state, upon electromyography data being transmitted from the myoelectric sensor 2, the masticatory side determination apparatus 1, in step S402, sequentially retrieves the digital signals SL and SR from the input/output interface unit 10 during a predetermined period of time, under the control of the data acquirer 21, and stores the signals in the electromyography data storage 31 in time series. The sampling rate can be set in the same manner as in the acquisition of learning data.

Next, in step S403, the processing unit 20 of the masticatory side determination apparatus 1 reads out pieces of electromyography data corresponding to the left and right temporalis muscles from the aforementioned electromyography data storage 31, and performs band-pass filtering on the pieces of data, under the control of the data processor 22.

(2-1-2) Calculation of Feature Values

Next, the masticatory side determination apparatus 1 calculates feature values under the control of the feature value calculator 23. In this embodiment, the three types of feature values that are that are the same as those used for learning, namely F1, F2, and F3, are calculated.

In step S404, under the control of the correlation coefficient calculator 231, the masticatory side determination apparatus 1 calculates the respective root mean squares (RMSs) of the pieces of electromyography data that correspond to the left and right temporalis muscles and have undergone filtering performed by the above-described data processor 22. Next, in step S405, the masticatory side determination apparatus 1 calculates, as the feature value F1, the coefficient of cross-correlation between the left and right RMSs, under the control of the correlation coefficient calculator 231.

The feature value calculator 23 of the masticatory side determination apparatus 1 can calculate the feature values F2 and F3 after carrying out steps S404 and S405 for calculating the aforementioned feature value F1, or in parallel with steps S404 and S405, or before carrying out steps S404 and S405.

In step S406, the masticatory side determination apparatus 1 performs frequency analysis such as FFT on each of the left and right pieces of electromyography data under the control of the right frequency parameter calculator 232 and the left frequency parameter calculator 233, to obtain the respective power spectra thereof.

Next, in step S407, the right frequency parameter calculator 232 and the left frequency parameter calculator 233 calculates the median power frequencies of the aforementioned power spectra as the feature values F2 and F3, respectively. Note that the right frequency parameter calculator 232 and the left frequency parameter calculator 233 can simultaneously or sequentially calculate the feature values F2 and F3 in steps S406 and S407.

The feature values F1, F2, and F3 calculated through the above-described processing are stored in the feature value storage 32 in step S408 together with time information.

(2-2) Determination of Abnormal Values

Next, in step S409, the masticatory side determination apparatus 1 reads out the learning model for abnormal value determination stored in the learning model storage 33 for abnormal value determination, and determines abnormal values with reference to the learning model, under the control of the abnormal value determiner 251. In this embodiment, whether or not each piece of data is a normal value or an abnormal value is determined using a learning model that has been established using the One-Class SVM. That is to say, as described above, the masticatory side determination apparatus 1 measures myoelectric potential data generated due to masticatory muscle activities, in advance as described above, and generates a learning model for abnormal value determination, based on the feature values calculated from the data. The masticatory side determination apparatus 1 determines whether or not newly measured data is a normal value or an abnormal value, i.e. a myoelectric potential or noise, with reference to the learning model generated in advance. If a feature value of newly measured data is within the boundary of the learning model, the newly measured data is determined as a myoelectric potential, and otherwise the newly measured data is determined as noise.

If the data is determined as a normal value (a myoelectric potential) in step S410 under the control of the abnormal value determiner 251, the masticatory side determination apparatus 1 transitions to step S411 and performs masticatory side determination processing. On the other hand, if the data is determined as an abnormal value (noise) in step S410, the masticatory side determination apparatus 1 can skip step S411. Note that steps S409 and S410 may be omitted. That is to say, the masticatory side determination apparatus 1 may perform class determination (masticatory side determination) on every piece of data without performing abnormal value determination.

(2-3) Determination of Masticatory Side

In step S411, the masticatory side determination apparatus 1 reads out the learning model for classification stored in the learning model storage 34 for classification, and determines the masticatory side with reference to the learning model, under the control of the class determiner 252. In this embodiment, the masticatory side determination apparatus 1 determines the class of each piece of data with reference to the learning model established using the k-nearest neighbors algorithm. That is to say, as described above, the masticatory side determination apparatus 1 measures, in advance, myoelectric potential data generated due to masticatory muscle activities, under such conditions that the masticatory side can be specified, as described above, and generates the learning model for classification by labeling the feature values calculated from the data. The class (the label) to which the newly measured data belongs, e.g. "bilateral mastication", "left side mastication", or "right side mastication", is determined with reference to the learning model.

Next, in step S412, the masticatory side determination apparatus 1 determines whether or not abnormal value determination (and class determination) have been performed on every piece of data. If any piece of data remains undetermined, the masticatory side determination apparatus 1 repeats the processing in steps S409 to S411 for such pieces of data.

(2-4) Output of Results of Determination

Upon determining in step S412 that no piece of data remains undetermined, the masticatory side determination apparatus 1 can aggregate and output the results of determination in step S413. For example, the masticatory side determination apparatus 1 can output the number or the proportion (%) of pieces of data classified into each of the labels of "bilateral mastication", "left side mastication", and "right side mastication" during a predetermined data acquisition period, via a display unit (not shown). The user (e.g. the subject themselves or a medical professional) seeing the results can estimate the degree of unilateral mastication of the subject. For example, if the data measured for a subject over a certain period of time shows the result of determination indicating that the proportion of pieces of data classified into right side mastication is significantly higher than those classified into left side mastication and bilateral mastication, it is possible to estimate that the subject is inclined to have right side unilateral mastication, and the user (e.g. the subject themselves or a medical professional) can take an appropriate measure such as having an examination to investigate the cause of unilateral mastication, making the subject aware of their masticatory habits, or prompting the subject to get treatment for cavities.

(Verification)

The effectiveness of determination performed by the masticatory side determination apparatus 1 according to one embodiment described above was verified. For this validation, ten subjects aged between 20 and 49 were selected. Two cloth electrodes were placed on each of the left and right temporalis muscles of each subject, and one ground electrode was placed on a central portion of the forehead of the subject. Each subject carried out the following five tasks in the state of sitting on a chair.

Task 1: perform bilateral mastication with chewing gum being placed on both the left and right sides of the mouth.

Task 2: perform unilateral mastication with chewing gum being placed only on the right side of the mouth.

Task 3: perform unilateral mastication with chewing gum being placed only on the left side of the mouth.

Task 4: perform voluntary blinking without moving the mouth.

Task 5: move the brim of the hat to the left and the right without moving the mouth.

Each task was continuously performed for one minute, and the myoelectric potentials of the left and right temporalis muscles were measured during this period. The sampling rate was set to 1000 Hz, and each subject performed the respective actions of the tasks at arbitrary intervals.

The feature values were calculated using the following method. A band-pass filter with the pass band of 20 Hz to 450 Hz (for removing body movement noise) and a notch filter for 50 Hz (for removing AC noise in a commercial power supply) were applied to the measurement data in each task. Regarding data that has undergone filtering, the respective root mean squares (RMSs) of the left and right sides were calculated using a time window of 100 ms, and a coefficient of correlation between the RMS values of the left and right sides was calculated using a time window of 2 s. Also, the median power frequency of the power spectrum was calculated for each of the left and right filtered values, using a time window of 2 s. Sample data for one second before and after the start point is used to calculate the feature values. Therefore, the number of samples of each feature value was 58000 for each task for each subject (data for 58 seconds from one second after the start to 59 seconds after the start was used).

Verification was performed using the One-Class SVM (v value: 0.9) as the algorithm for abnormality detection, data of Task 1 as learning data, and data of Tasks 2 to 5 as test data. The feature values F1, F2, and F3 calculated from the measurement data of Task 1 were subjected to pre-processing for standardization, and thereafter a learning model for abnormal value determination was established using the One-Class SVM. Thereafter, the learning model was applied to each test data sample, each sample was subjected to determination performed to discern between a myoelectric potential and noise, and the proportion of each was measured.

Figure 5:
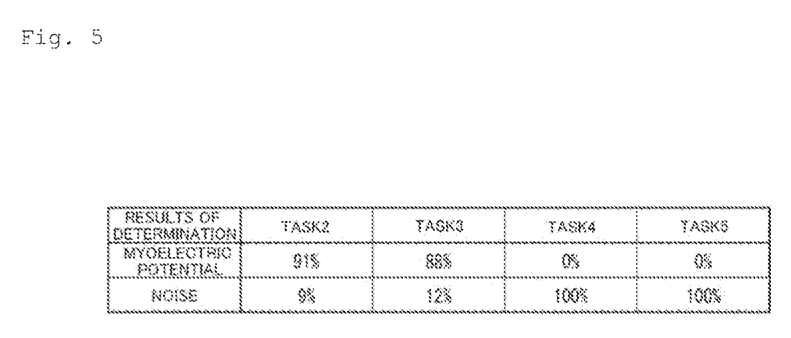
FIG. 5 is a diagram showing the result of verification of abnormal value determination performed using a masticatory side determination apparatus according to one embodiment of the present disclosure.

FIG. 5 shows the results of abnormal value determination performed for ten subjects, obtained through the aforementioned verification. As described above, data regarding Task 1 corresponding to bilateral masticatory actions was used as learning data. It can be seen from the results that, regarding Tasks 2 and 3 corresponding unilateral masticatory actions, the probability of myoelectric potentials being correctly determined as myoelectric potentials was approximately 90%, and regarding Tasks 4 and 5 that are not masticatory actions, the probability of noise being determined as noise was 100%. Therefore, by using the above-described embodiment, it is possible to accurately discern between myoelectric potentials and noise, and it is possible to perform a reliable masticatory side determination based on myoelectric potential by removing the data determined as noise, and only analyzing the data determined as myoelectric potentials.

Next, in order to check the accuracy in determining the masticatory side, the determination accuracy was measured though 10-fold cross validation, only using the data of Tasks 1, 2, and 3. Cross validation is validation through which data of each class is divided into n groups, n−1 groups are used as learning data, and the remaining one group is used as test data. Generally, the average of validation repeated n times using different groups of test data is used as the result of validation. Here, data of all of Tasks 1 to 3 were divided into 10 groups and were subjected to cross validation. The feature values were the same as the three type of feature values used in the aforementioned abnormality detection. The k-nearest neighbors algorithm was used as the machine learning algorithm for classification (the number of nearest neighbors to be detected: five), and pre-processing for standardization was performed on each feature value. Three type of labels, namely bilateral mastication, right side mastication, and left side mastication, were used.

Figure 6:
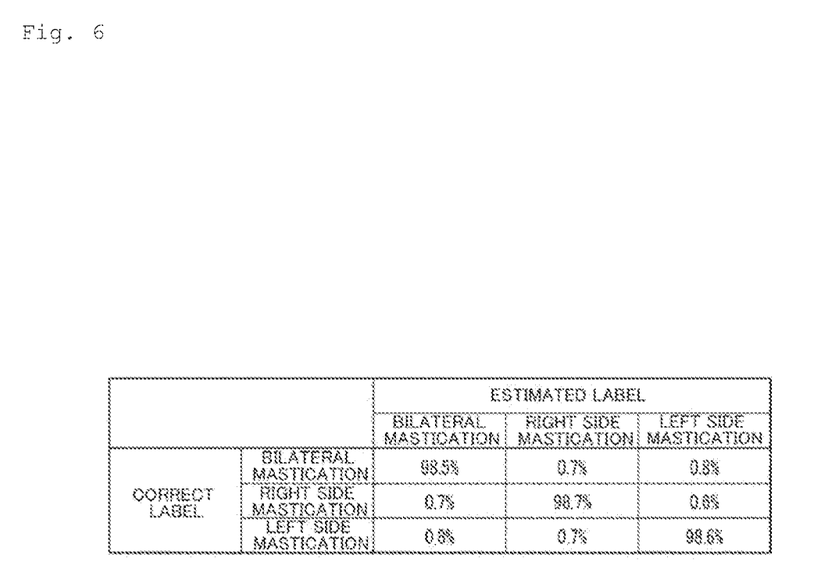
FIG. 6 is a diagram showing the result of verification of masticatory side determination performed using a masticatory side determination apparatus according to one embodiment of the present disclosure.

FIG. 6 shows the proportions of the labels resulting from the determination regarding the tasks, obtained through the above-described verification. The pieces of data in the upper tier, to which the correct label "bilateral mastication" is attached, shows that 98.5% of data were classified into bilateral mastication, 0.7% into right side mastication, and 0.8% into left side mastication. Thus, bilateral mastication was correctly discerned with a high probability of 98.5%. The pieces of data in the middle tier and the lower tier were also correctly classified with a high probability of approximately 99%. As described above, by only using data originating from myoelectric potentials in masticatory side determination, it is possible to accurately estimate the masticatory side.

It can be seen from the above-described results of verification that it is possible to perform accurate and reliable masticatory side determination that is robust to body move noise, by first determining whether a given piece of data is a myoelectric potential or noise, and thereafter performing masticatory side determination only on pieces of data determined as myoelectric potentials.

During masticatory actions, the left and right temporomandibular joints move at the same time, and therefore it is envisaged that the correlation coefficient, which is the feature value F1, of bilateral mastication (Task 1) and that of unilateral mastication (Tasks 2 and 3) are not significantly different from each other. However, in the cases of Tasks 4 and 5, although the temporalis muscles substantially do not perform any action, noise components originating from movement of muscles in other portions are superimposed on the measured myoelectric potentials. In contrast to masticatory actions, such noise components are often asymmetrical. Therefore, the coefficient of correlation between the left and right sides is low, and it is envisaged that the feature value 1 of Tasks 1 to 3 and that of Tasks 4 and 5 are significantly different from each other.

In addition, although the median power frequencies of the power spectra, which are feature values F2 and F3, can be considered as indicators of the characteristics of muscle activities, they vary significantly from individual to individual, and it is not easy to generalize and define the correspondence relationship with the masticatory side. However, it has been found that it is possible to obtain accurate results of determination by using machine learning as described above.

Although the One-Class SVM, which is an unsupervised learner, is used to perform abnormality detection, i.e. determination to distinguish a myoelectric potential and noise, in the above-described embodiment, another method may be used instead. For example, abnormality detection according to the Hotelling's theory that is based on statistical models or the k-nearest neighbors algorithm that is based on the distance between pieces of data may be used.

(Effects)

As described above in detail, the masticatory side determination apparatus 1 according to one embodiment acquires pieces of data indicating the surface electromyographies (sEMGs) of the left and right temporalis muscles, performs predetermined filtering on these pieces of data, and thereafter calculate the three types of feature values as described above. Based on these feature values, the masticatory side determination apparatus 1 generates a learning model for abnormal value determination and a learning model for classification, discerns between an abnormal value and a normal value, with reference to each learning model, and subsequently performs class determination on only on the pieces of data determined as normal values.

Through the verification experiment, it was found that the above-described masticatory side determination apparatus 1 was able to perform accurate abnormal value detection and class determination. It can be considered that the above-described masticatory side determination apparatus 1 was able to perform learning and determination that are relatively robust to changes in skin impedance because information regarding the amplitudes of the muscle potentials, which are susceptible to skin impedance, was not selected as a feature value. Also, it can be considered that the above-described masticatory side determination apparatus 1 was able to perform reliable determination based on data that includes less noise such as body movement noise because the pieces of data determined as abnormal values were excluded and only the pieces of data determined as normal values were used to perform class determination.

As described above, by generating learning models, using the above-described three types of feature values, and performing abnormal value determination with reference to the learning models, the above-described masticatory side determination apparatus 1 can accurately perform determination to decern between a myoelectric potential and noise. Also, using the results of determination, the above-described masticatory side determination apparatus 1 subsequently determines the masticatory side by only analyzing myoelectric potentials. Thus, the masticatory side determination apparatus 1 can reliably determine the masticatory side. Furthermore, by removing noise in advance, it is possible to reduce the processing load on the system related to class determination. By using learning and determination that are relatively robust to changes in skin impedance, it is possible to more accurately and reliably reveal the user's mastication habits in daily life than when only the amplitudes of myoelectric potentials are used.

The activities of the masticatory muscles are related to the movement of closing the jaw, and the motion is simple and the waveforms of the muscle potentials thereof are similar to each other. Therefore, it is possible to generate learning models by only using a small amount of training data as described above. On the other hand, various factors may cause noise, and the waveforms of potential changes caused by noise are also various. Therefore, it is envisaged that it is impossible to comprehensively learn all of them. With the method described in the above embodiment, it is possible to accurately determine the masticatory side by performing simple processing, without placing an excessive load on the subject, or placing an excessive load on the system.

Furthermore, since the method according to the above-described embodiment does not require an additional function of a myoelectric sensor itself, it is possible to use an existing myoelectric sensor without change to implement the above-described embodiment.

Other Embodiments

The above embodiment describes a case in which the generation of learning models, the determination of abnormal values, and the determination of the masticatory side are performed using a coefficient of correlation between the absolute values of the left and right myoelectric potentials in a constant window range, the median power frequency of the power spectrum of the right myoelectric potential in the constant window range, and the median power frequency of the power spectrum of the left myoelectric potential in the constant window range, as three feature values F1, F2, and F3. However, feature values are not limited to these values, and any kind of information, such as a coefficient of correlation between the shapes of waveforms, the average frequency of the power spectrum, or a signal strength related to a particular frequency component may also be used as feature values.

In addition, the above embodiment describes a case in which movements of the left and right temporalis muscles are measured in order to analyze masticatory actions. However, the present invention is not limited to such a case. In addition to temporalis muscles, the left and right masseter muscles located near the back teeth also move together during masticatory actions, and therefore the surface electromyographies (sEMGs) thereof can be measured using the same processing procedure.

In addition to masticatory actions, the present invention is also applicable to other actions during which the muscles move together symmetrically, such as bending and stretching. The present invention can also be carried out even if the configuration of the myoelectric sensor, the procedure and the content of processing performed to measure the surface electromyography, the threshold values, and the like are variously modified without departing from the scope of the present invention.

Although the above embodiment describes a case in which the acquisition of data and the calculation of feature values are performed by the same functional unit in learning model generation processing and in determination processing, it is possible to provide an independent functional unit for each processing.

Furthermore, although the above embodiment describes a masticatory side determination apparatus 1 that includes both the learning model generation unit and the determination unit, the present invention is not limited to such a configuration, and the masticatory side determination apparatus 1 may include only one of these units. In such a case, a determination apparatus that only includes the determination unit can read out learning models that have been generated in advance, from an internal or external storage apparatus or the like, and reference them when performing determination. Furthermore, it is possible that the masticatory side determination apparatus 1 does not perform abnormal value determination, and performs class determination on all of the acquired pieces of data. In such a case, it is possible to improve the accuracy of determination by appropriately performing filtering in advance.

In summary, the present invention is not necessarily limited to the above embodiment without change, and the constituent elements of the present invention may be modified without departing the spirit thereof when carried out. Also, various inventions may be formed by appropriately combining the plurality of constituent elements disclosed in the above embodiment. For example, one or more constituent elements may be deleted from the constituent elements shown in the embodiment. Furthermore, constituent elements shown in different embodiments may be combined with each other as appropriate.

REFERENCE SIGNS LIST

1 Masticatory Side Determination Apparatus
2 Myoelectric Sensor
3G, 3L, 3R Electrode
10 Interface Unit
20 Processing Unit
21 Data Acquirer
22 Data Processor
23 Feature Value Calculator
24 Learning Model Generator
25 Determiner
30 Storage Unit
31 Electromyography Data Storage
32 Feature Value Storage
33 Learning Model Storage for Abnormal Value Determination
34 Learning Model Storage for Classification
231 Correlation Coefficient Calculator
232 Right Frequency Parameter Calculator
233 Left Frequency Parameter Calculator
241 Abnormal Value Determination Learning Model Generator
242 Classification Learning Model Generator
251 Abnormal Value Determiner
252 Class Determiner

The invention claimed is:

1. A masticatory side determination apparatus that determines a masticatory side of a user, the masticatory side determination apparatus comprising:
a processor; and
a storage medium having computer program instructions stored thereon, when executed by the processor, perform to:
acquire first and second electromyographic waveforms respectively originating from left and right muscles related to masticatory actions of the user;
calculate a first feature value as a coefficient of correlation between pieces of information respectively extracted from the first and the second electromyographic waveforms, the coefficient of correlation being a cross-coefficient of correlation between absolute values of potentials determined based on root mean squared (RMS) processing of the first and second electromyographic waveforms;
calculate a second feature value from a power spectrum obtained by performing frequency analysis on the first electromyographic waveform, the second feature value being a median power frequency from the power spectrum of the first electromyographic waveform;
calculate a third feature value from a power spectrum obtained by performing frequency analysis on the second electromyographic waveform, the third feature value being a median power frequency from the power spectrum of the second electromyographic waveform; and
generate a learning model based on the first, second, and third feature values; and determine the masticatory side of the user using the learning model, based on the first, second, and third feature values.

2. The masticatory side determination apparatus according to claim 1, wherein the computer program instructions further perform to determine whether the first, second, and third feature values are normal values or abnormal values for each predetermined unit time range, based on the first, the second, and the third feature values, and performs masticatory side determination only for a unit time range in which the feature values are determined as normal values.

3. The masticatory side determination apparatus according to claim 2, wherein the computer program instructions use an unsupervised learning model to perform abnormal value determination.

4. A non-transitory computer-readable medium having computer-executable instructions that, upon execution of the instructions by a processor of a computer, cause the computer to function as the masticatory side determination apparatus of claim 1.

5. A learning model generation method that is carried out by a learning model generation apparatus, comprising:

acquiring first and second electromyographic waveforms respectively originating from left and right muscles related to masticatory actions of a user;

calculating a first feature value as a coefficient of correlation between pieces of information respectively extracted from the first and the second electromyographic waveforms, the coefficient of correlation being a cross-coefficient of correlation between absolute values of potentials determined based on root mean squared (RMS) processing of the first and second electromyographic waveforms;

calculating a second feature value for learning, from a power spectrum obtained by performing frequency analysis on the first electromyographic waveform, the second feature value being a median power frequency from the power spectrum of the first electromyographic waveform;

calculating a third feature value for learning, from a power spectrum obtained by performing frequency analysis on the second electromyographic waveform, the third feature value being a median power frequency from the power spectrum of the second electromyographic waveform;

generating a learning model based on the first, second, and third feature values and a plurality of labels for specifying a masticatory side of the user; and determining the masticatory side of the user using the learning model, based on the first, second, and third feature values.

* * * * *